(12) United States Patent
Cao et al.

(10) Patent No.: US 12,385,823 B2
(45) Date of Patent: Aug. 12, 2025

(54) EVALUATION METHOD FOR CORROSION DAMAGE EVOLUTION OF UNDERWATER CONCRETE STRUCTURES

(71) Applicants: Hohai University, Nanjing (CN); Jiangxi University of Science and Technology, Ganzhou (CN); Jiangsu Dongjiao Intelligent Control Technology Group Co., Ltd., Nanjing (CN)

(72) Inventors: Maosen Cao, Nanjing (CN); Li Wei, Nanjing (CN); Jie Wang, Nanjing (CN); Tongfa Deng, Ganzhou (CN); Dragoslav Sumarac, Nanjing (CN); Xiangdong Qian, Nanjing (CN); Lei Shen, Nanjing (CN); Nizar Faisal Alkayem, Nanjing (CN); Drahomir Novak, Nanjing (CN)

(73) Assignees: Hohai University, Nanjing (CN); Jiangxi University of Science and Technology, Ganzhou (CN); Jiangsu Dongjiao Intelligent Control Technology Group Co., Ltd., Nanjing (CN)

( * ) Notice: Subject to any disclaimer, the term of this patent is extended or adjusted under 35 U.S.C. 154(b) by 340 days.

(21) Appl. No.: 18/201,782

(22) Filed: May 25, 2023

(65) Prior Publication Data
US 2023/0384209 A1    Nov. 30, 2023

(30) Foreign Application Priority Data

May 25, 2022   (CN) .......................... 202210574972.6

(51) Int. Cl.
*G01N 17/00*    (2006.01)
*G01N 3/08*    (2006.01)
(Continued)

(52) U.S. Cl.
CPC ............. *G01N 17/008* (2013.01); *G01N 3/08* (2013.01); *G01N 3/32* (2013.01); *G01N 29/04* (2013.01);
(Continued)

(58) Field of Classification Search
CPC .......... G01N 17/008; G01N 3/08; G01N 3/32; G01N 2203/0019; G01N 2203/0073;
(Continued)

(56) References Cited

U.S. PATENT DOCUMENTS 8,176,786 B2 *   5/2012  Sohn .................. G01N 29/2475
                                                            73/598

OTHER PUBLICATIONS

Huang et al., "Influence of HCl corrosion on the mechanical properties of concrete", Cement and Concrete Research, vol. 35, 2005, <https://www.sciencedirect.com/science/article/abs/pii/S0008884604002807> (Year: 2005).*
(Continued)

*Primary Examiner* — Jonathan M Dunlap
(74) *Attorney, Agent, or Firm* — Bayramoglu Law Offices LLC

(57) ABSTRACT

An evaluation method for corrosion damage evolution of underwater concrete structures includes performing the time reversal test on the concrete beam specimen placed in the water, performing the uniaxial compression test on the concrete cube specimens; immersing the concrete beam specimen and the concrete cube specimens in a hydrochloric acid solution, and performing the time reversal test on the concrete beam specimen on the 10th, 20th and 30th days respectively. At the same time, a concrete cube specimen is taken out to perform the uniaxial compression test on the 10th, 20th and 30th days respectively; and using the above
(Continued)

calculation results to evaluate the corrosion evolution process thereof without damaging the underwater concrete structure.

3 Claims, 7 Drawing Sheets

(51) Int. Cl.
    *G01N 3/32* (2006.01)
    *G01N 29/04* (2006.01)
(52) U.S. Cl.
    CPC ............... *G01N 2203/0019* (2013.01); *G01N 2203/0073* (2013.01); *G01N 2203/024* (2013.01)
(58) Field of Classification Search
    CPC ..... G01N 2203/024; G01N 2203/0218; G01N 2203/0236; G01N 2203/0252; G01N 2203/0298; G01N 2203/0617; G01N 2203/0676; G01N 2203/0688; G01N 2203/0003; G01N 33/383; G01N 29/04; G01N 29/44
    See application file for complete search history.

(56) References Cited

OTHER PUBLICATIONS

Olusola et al., "Effect of Nitric Acid Concentration on the Compressive Strength of Laterized Concrete", Civil and Environmental Research, vol. 2, No. 10, 2012, <https://www.iiste.org/Journals/index.php/CER/article/download/3539/3587> (Year: 2012).*

Hasan et al., "Mechanical Properties of Concrete in Compression Exposed to Sulfuric Acid", Key Engineering Materials, vol. 711, Sep. 2016, pp. 302-309 <https://doi.org/10.4028/www.scientific.net/kem.711.302> (Year: 2016).*

* cited by examiner

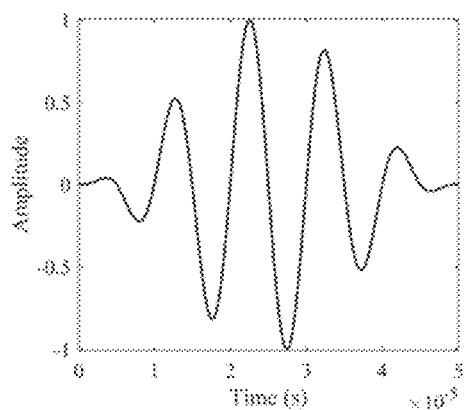
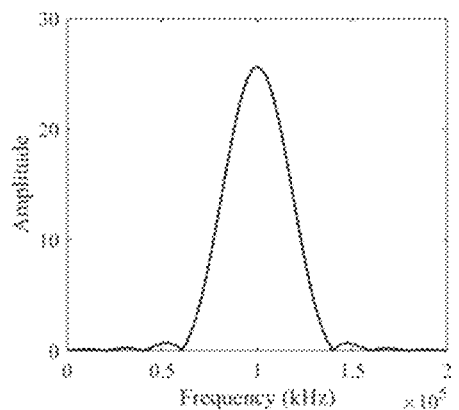
FIG. 8A  FIG. 8B
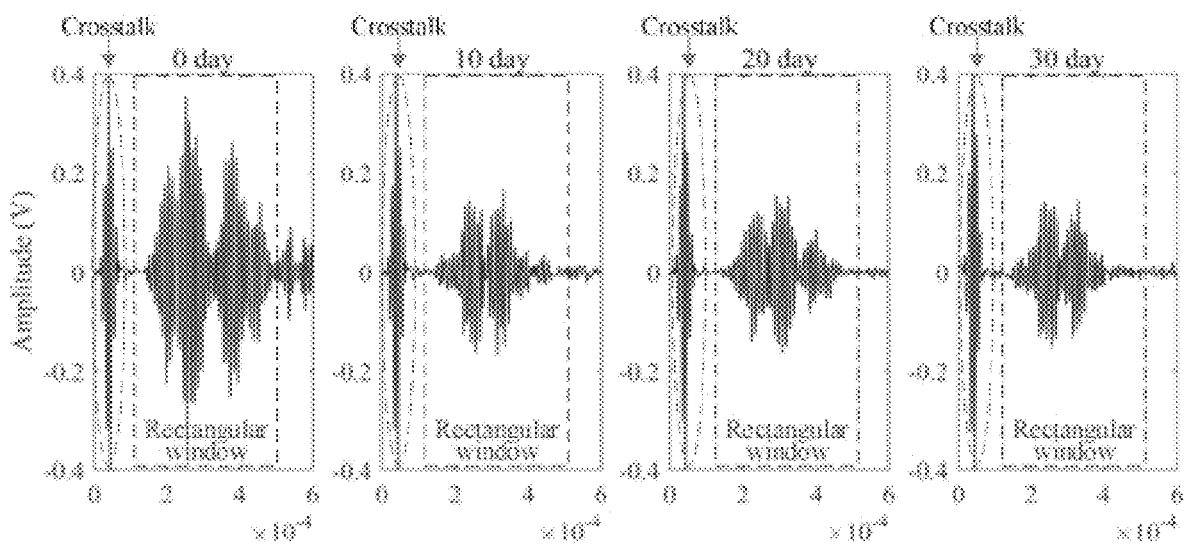
FIG. 9A  FIG. 9B  FIG. 9C  FIG. 9D
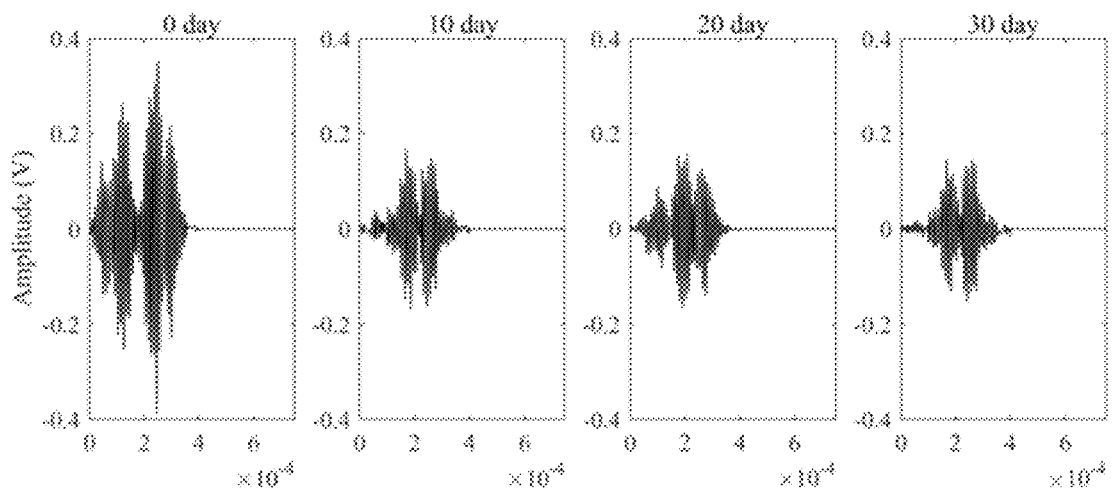
FIG. 10A  FIG. 10B  FIG. 10C  FIG. 10D

EVALUATION METHOD FOR CORROSION DAMAGE EVOLUTION OF UNDERWATER CONCRETE STRUCTURES

CROSS REFERENCE TO THE RELATED APPLICATIONS

This application is based upon and claims priority to Chinese Patent Application No. 202210574972.6, filed on May 25, 2022, the entire contents of which are incorporated herein by reference.

TECHNICAL FIELD

The present invention belongs to the technical field of nondestructive testing, and particularly relates to an evaluation method for corrosion damage evolution of underwater concrete structures.

BACKGROUND ART

Underwater concrete structures (such as bridge piers, dams and underwater concrete pipes) are usually built as important load-bearing members in concrete constructions. They suffer from various damage due to the complex service environment, especially the long-term physical erosion and chemical corrosion of water. These water erosion and corrosion can induce damage to underwater concrete structures, resulting in the degradation of their local mechanical properties. These kinds of damage may become a major factor that affects structures' safety, applicability, and durability. In this regard, it is significant to develop an evaluation method for corrosion damage evolution of underwater concrete structures.

At present, acoustic imaging-based methods and optical imaging-based methods are generally adopted to evaluate the damage of underwater concrete structures. Among them, the optical imaging-based methods mainly include artificial diving photography, underwater photographing robot, etc., and the acoustic imaging-based methods include acoustic emission, sonar, etc. However, these methods have the following limitations: (1) the measured data is susceptible to water quality; (2) the underwater flow situation is complicated, and sometimes the measurement equipment cannot be well placed at the predetermined position; (3) the equipment is expensive and measurement is time-consuming; and (4) it is difficult to detect the global damage and internal damage of structures. These limitations make these methods difficult to apply to evaluate the corrosion damage of underwater concrete structures.

In recent years, a time reversal method based on stress waves is widely used in the damage evaluation of concrete structures because of its self-adapting spatial, temporal focusing characteristics, high signal-to-noise ratio, and suitability for heterogeneous materials. The results show that the time reversal method based on stress waves can be used to identify and locate the damage in concrete structures, but the feasibility of applying the time reversal method based on stress waves to evaluate the corrosion damage of underwater concrete structures still lacks proof.

SUMMARY

In view of this, the present invention provides an evaluation method for corrosion damage evolution of underwater concrete structures in order to solve the technical problems mentioned above. The present invention belongs to the field of nondestructive testing of underwater concrete structures, especially related to the corrosion damage caused by hydrochloric acid to underwater concrete structures, which provides a feasible method for corrosion damage evolution of underwater concrete structures based on the time reversal of stress waves.

The technical solution of the present invention is as follows:

The evaluation method for corrosion damage evolution of underwater concrete structures includes:

(a) immersing a concrete beam specimen and concrete cube specimens in water;

(b) performing a time reversal test on the concrete beam specimen placed in the water to obtain a damage index $DI^0$ of concrete in a water-immersed state, performing a uniaxial compression test on the concrete cube specimens to obtain a compressive strength $F_{cp}^0$ and an elastic modulus $E_c^0$ of concrete in the water-immersed state;

(c) immersing the concrete beam specimen and concrete cube specimens in a hydrochloric acid solution to mimic the long-term corrosion damage of concrete underwater. Performing the time reversal test on the concrete beam specimens placed in the hydrochloric acid solution on the 10th, 20th and 30th days respectively to obtain a damage index DI' of concrete in the corrosion state. At the same time. On the 10th, 20th and 30th days, a concrete cube specimen is taken out to perform the uniaxial compression test to obtain a compressive strength $F'_{cp}$ and an elastic modulus $E'_c$ of concrete in the corrosion state.

(d) calculating a corrosion index CI with formula (1), calculating a compressive strength loss rate $LR_F$ with formula (2), calculating an elastic modulus loss rate $LR_E$ with formula (3), and $$CI = DI' - DI^0 \tag{1}$$

$$LR_F = \frac{F_{cp}^0 - F'_{cp}}{F_{cp}^0} \tag{2}$$

$$LR_E = \frac{E_c^0 - E'_c}{E_c^0} \tag{3}$$

In the formulas, CI is the corrosion index, $DI^0$ is the damage index of concrete in the water-immersed state, DI' is the damage index of concrete in the corrosion state, $LR_F$ is the loss rate of concrete compressive strength, $F_{cp}^0$ is the compressive strength of concrete in the water-immersed state, $F'_{cp}$ is the compressive strength of concrete in the corrosion state, $LR_E$ is the loss rate of concrete elastic modulus, $E_c^0$ is the elastic modulus of concrete in the water-immersed state, and $E'_c$ is the elastic modulus of concrete in the corrosion state; and (e) calculating an absolute error between the corrosion index and the loss rate of concrete compressive strength with formula (4), and calculating an absolute error between the corrosion index and the loss rate of concrete elastic modulus with formula (5), so as to realize evaluation of corrosion damage evolution of the underwater concrete structures;

$$\delta_{CE} = CI - LR_F \tag{4}$$

$$\delta_{CE} = CI - LR_E \tag{5}$$

In the formulas, $\delta_{CF}$ is the absolute error between the corrosion index and the loss rate of concrete compressive strength, CI is the corrosion index, $LR_F$ is the loss rate of concrete compressive strength, $\delta_{CE}$ is the absolute error between the corrosion index and the loss rate of concrete elastic modulus, and $LR_E$ is the loss rate of concrete elastic modulus.

Preferably, a method for obtaining the damage index of concrete by performing the time reversal test on the concrete beam specimen includes:

(21) determining an excitation signal $V_A(t)$;

(22) inputting the excitation signal $V_A(t)$ to a sensor ⑤ at A on the concrete beam specimen, expression of response signals received by a sensor ⑥ at B in frequency domain is formula (6), $$V_B(r,\omega)=k_A(\omega)k_B(\omega)G(r,\omega)V_A(W) \quad (6)$$

the expression of the response signals in time domain is formula (7), $$V_B(t) = \frac{1}{2\pi}\int_{-\infty}^{+\infty} V_B(r,\omega)e^{i\omega t}d\omega \quad (7)$$

In the formula, r is a distance from A to B, $k_A$ is an electromechanical coupling coefficient of the sensor ⑤ at A, $k_B$ is an electromechanical coupling coefficient of the sensor ⑥ at B, and $G(r, \omega)$ is a transfer function from the sensor ⑤ at A to the sensor ⑥ at B; $V_B(t)$ is the response signal received by the sensor ⑥ at B;

(23) after applying a rectangular window, as shown in formula (8), to the response signal to remove crosstalk, and then the time reversal is performed to obtain a reversed signal, $$w(t) = \begin{cases} 1, & 0 \le t \le T \\ 0, & \text{else} \end{cases} \quad (8)$$

the expression of the reversed signal in frequency domain is formula (9), $$\hat{V}_B(r,\omega)=k^*_A(\omega)k^*_B(\omega)G^*(r,\omega)V^*_A(\omega)e^{i\omega T} \quad (9)$$

the expression of the reversed signal in time domain is formula (10), $$V_B(-t) = \frac{1}{2\pi}\int_{-\infty}^{+\infty} V_B^+(r,\omega)e^{i\omega T}e^{i\omega t}d\omega \quad (10)$$

In the formulas, $V^*_B$ is a phase conjugation of $V_B$, * is a complex conjugation operator, T is a sampling duration, and r is the distance from A to B;

(24) inputting the reversed signal to the sensor ⑥ at B, then the sensor ⑤ at A receives a focused signal, the expression of the focused signal in frequency domain is formula (11), and $$\hat{V}_A(r,\omega)=k_A(\omega)k^*_A(\omega)k_B(\omega)k^*_B(\omega)G(r,\omega)G^*(r,\omega)V^*_A(\omega)e^{i\omega T} \quad (11)$$

the expression of the focused signal in time domain is formula (12);

$$\hat{V}_A(t) = \frac{1}{2\pi}\int_{-\infty}^{+\infty} \hat{V}_A(r,\omega)e^{i\omega t}d\omega$$

$$= \frac{1}{2\pi}\int_{-\infty}^{+\infty} k_A(\omega)k^*_A(\omega)k_B(\omega)k^*_B(\omega)G(r,\omega)G^*(r,\omega) \quad (12)$$

$$V^*_A(\omega)e^{i\omega T}e^{i\omega t}d\omega$$

(25) performing time reversal reconstruction on the focused signal to obtain a reconstructed signal, and the expression of the reconstructed signal in frequency domain is formula (13), $$\tilde{V}_A(r,\omega)=\hat{V}^*_A(r,\omega)e^{i\omega T} \quad (13)$$

In the formula, $\hat{V}^*_A$ is a phase conjugation of $\hat{V}_A$, and * is the complex conjugation operator; and the expression of the reconstructed signal in time domain is formula (14);

$$\tilde{V}_A(t) = \frac{1}{2\pi}\int_{-\infty}^{+\infty} \hat{V}^*_A(r,\omega)e^{i\omega T}e^{i\omega t}d\omega \quad (14)$$

$$= \frac{1}{2\pi}\int_{-\infty}^{+\infty} k_A(\omega)k_B(\omega)k^*_A(\omega)k^*_B(\omega)G(r,\omega)G^*(r,\omega)$$

$$V_A(\omega)e^{i\omega t}d\omega$$

(26) performing normalization on the excitation signal and the reconstructed signal with formula (15), $$N_A(t)=V_A(t)/\max(V_A(t))$$

$$\tilde{N}_A(t)=\tilde{V}_A(t)/\max(\tilde{V}_A(t)) \quad (15)$$

In the formulas, $V_A(t)$ is the excitation signal, $\tilde{V}_A$ is the reconstructed signal, $N_A$ is the normalized excitation signal, and $\tilde{N}_A$ is the normalized reconstructed signal; and

(27) substituting the normalized excitation signal and the normalized reconstructed signal into formula (16) to calculate the damage index;

$$DI = \qquad\qquad\qquad\qquad\qquad\qquad\qquad\qquad\qquad (16)$$

$$1 - \sqrt{\left[\int_{t_0}^{t_1} N_A(t)\tilde{N}_A(t)dt\right]^2 \bigg/ \int_{t_0}^{t_1}[N_A(t)]^2 dt \int_{t_0}^{t_1}[\tilde{N}_A(t)]^2 dt} \times 100\%$$

In the formula, DI is the damage index, $t_0$ and $t_1$ are start time and end time of a signal comparison interval separately, $N_A(t)$ is the normalized excitation signal, and $N_A(t)$ is the normalized reconstructed signal.

Preferably, a method for determining the excitation signal $V_A(t)$ includes:

The expression of a 5-cycle sine function modulated by a Hanning window is formula (17), $$x(t) = \sin(2\pi f_c t)\left[1 - \cos\frac{2\pi f_c t}{5}\right] \quad (17)$$

In the formula, $f_c$ is central frequency of the modulated signals;

A method for determining the central frequency of the modulated signals is as follows:

modulated signals with different central frequencies are modulated from 0-10 MHz at an interval of 10 kHz, the modulated signals with different central frequencies are input to the sensor ⑤ at A on the concrete beam specimen separately, and the response signals are received by the sensor ⑥ at B, the modulated signal with the largest amplitude of the response signal is selected as the excitation signal $V_A(t)$.

Preferably, the compressive strength of concrete in the water-immersed state is obtained with formula (18), and the elastic modulus of concrete in the water-immersed state is obtained with formula (19);

$$F_{cp} = \frac{F_{max}}{A} \quad (18)$$

$$E_c = \frac{(F_a - F_0)}{A} \times \frac{L}{\Delta} \quad (19)$$

In the formulas, $F_{cp}$ is the compressive strength of the concrete cube specimen, $F_{max}$ is a failure load, A is a loading area of the specimen, $E_c$ is the elastic modulus of the concrete cube specimen, $F_a$ is a load when stress is ⅔$F_{cp}$, $F_0$ is a load when the stress is ⅓$F_{cp}$, L is a measuring scale distance of the concrete cube specimen, and $\Delta$ is a deformation of the concrete cube specimen loaded from $F_0$ to $F_a$.

Preferably, a method for preparing the concrete specimens includes:

performing anti-corrosion, insulation and waterproof treatment on a pair of sensors;

building a formwork of the concrete specimens;

placing sensors at predetermined positions in the formwork of the concrete beam specimen; and pouring concrete, and completing maintenance according to standards.

Compared with the existing technology, the evaluation method for the corrosion damage evolution of underwater concrete structures provided by the present invention has advantages that the method is not easily affected by water quality, the sensor arrangement is simple, the integrity damage of underwater concrete structures can be detected, and the corrosion evolution process can be evaluated without damaging underwater concrete structures, and the method is practical and worth popularizing.

BRIEF DESCRIPTION OF THE DRAWINGS

In order to describe the examples and the technical solutions of the present invention, accompanying drawings required by the examples are briefly introduced below. Obviously, the accompanying drawings in the following description are only partial examples of the present invention, and a person of ordinary skill in the art can be able to derive other accompanying drawings from these accompanying drawings without creative efforts. According to the examples of the present invention, corrosion evolution of underwater concrete structures is evaluated by taking corrosion damage caused by immersing C30 concrete specimens in a hydrochloric acid solution with pH=1 as an example.

FIGS. 8A-8B are the excitation signals with a central frequency of 100 kHz selected in the present invention: (a) time domain diagram; (b) frequency domain diagram;

FIGS. 9A-9D are diagrams of the response signal obtained by performing the time reversal test on the concrete beam specimen at different corrosion durations in the present invention;

FIGS. 10A-10D are diagrams of the reversed signal obtained by performing the time reversal test on the concrete beam specimen at different corrosion durations in the present invention;

DETAILED DESCRIPTION OF THE EMBODIMENTS

In order to make the technical solution of the present invention better understood and implemented by those skilled in the art, the present invention will be described in detail below with reference to FIG. 1-FIG. 13. The following examples are only illustrative of the technical solution of the present invention more clearly and are not intended to limit the scope of protection of the present invention.

Example 1

Figure 1:
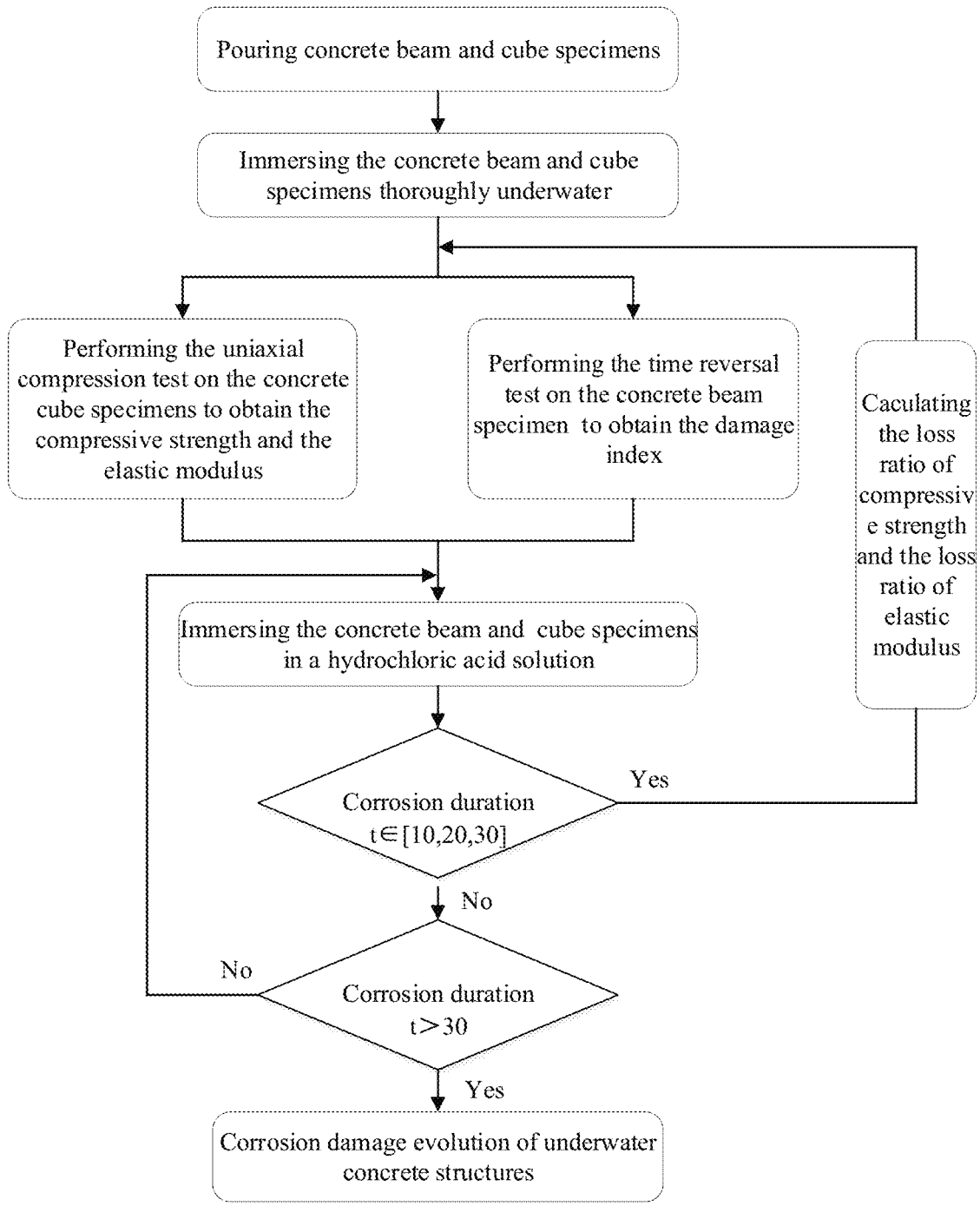
FIG. 1 is a flow chart of a method in the present invention.
Figure 2:
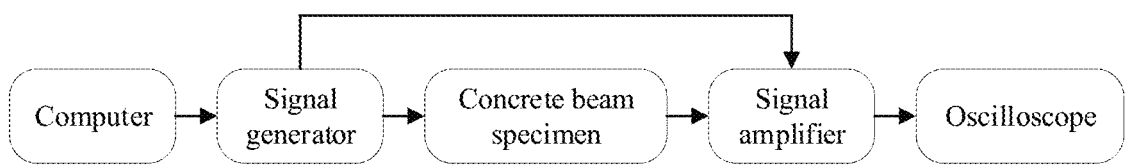
FIG. 2 is a schematic diagram of a time reversal test system for a concrete beam specimen in the present invention.

According to the evaluation method for corrosion damage evolution of underwater concrete structures, the basic steps are shown in the flow chart of FIG. 1. The time reversal test system of the concrete beam specimen in the present example is shown in FIG. 2, the time reversal test system is composed of a computer, a signal generator, a signal amplifier and an oscilloscope, before the time reversal test, the computer is connected to the signal generator, the signal generator is connected to the oscilloscope, the oscilloscope is connected to the signal amplifier, clamps are led out from the signal amplifier and the signal generator respectively, and are connected to the concrete beam specimen in the experiment to perform the time reversal test. An anti-corrosion tank is filled with water/hydrochloric acid, which is capable to immerse the concrete specimen.

Figure 3:
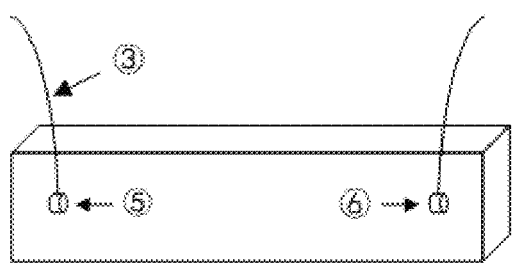
FIG. 3 is a schematic diagram of the concrete beam specimen in the present invention.
Figure 4:
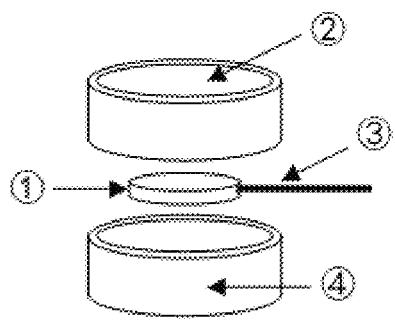
FIG. 4 is a schematic diagram of sensors in the present invention.

The present invention will be further described with reference to FIG. 1 and a test process:

(1) the method for preparing the concrete specimens includes:

performing anti-corrosion, insulation and waterproof treatment on a pair of sensors, with a specific operation method as shown in FIG. 4: selecting $d_{33}$-type PZT patches ① having a diameter of 14 mm and a thickness of 1 mm for the sensors, and encapsulating the $d_{33}$-type PZT patches with an acrylic pipe ④ having an external diameter of 25 mm, a wall thickness of 2 mm and a height of 20 mm and epoxy resin adhesive ②, and leading out leads ③ to achieve the objectives of anti-corrosion, insulation and waterproof;

after that, building a formwork of the concrete beam specimen, placing the sensors at predetermined positions A and B in the formwork, after leading out the leads ③, pouring concrete, and making C30 concrete specimen by selecting ordinary Portland cement with a grade of 32.5, fine aggregates are sands with particle sizes of 0.25-0.5 mm, and coarse aggregates are stones with particle sizes of 5-30 mm according to a mass ratio of 1:0.958:2.462 and a water-cement ratio of 0.38. As shown in FIG. 3, the size of the concrete beam specimen is 500 mm×100 mm×100 mm (length×width×height), the size of concrete cube specimens is 100 mm×100 mm×100 mm, the two sensors are located on the longitudinal axis line 20 mm away from the left and right ends respectively, and maintenance is completed according to standards.

Figure 5:
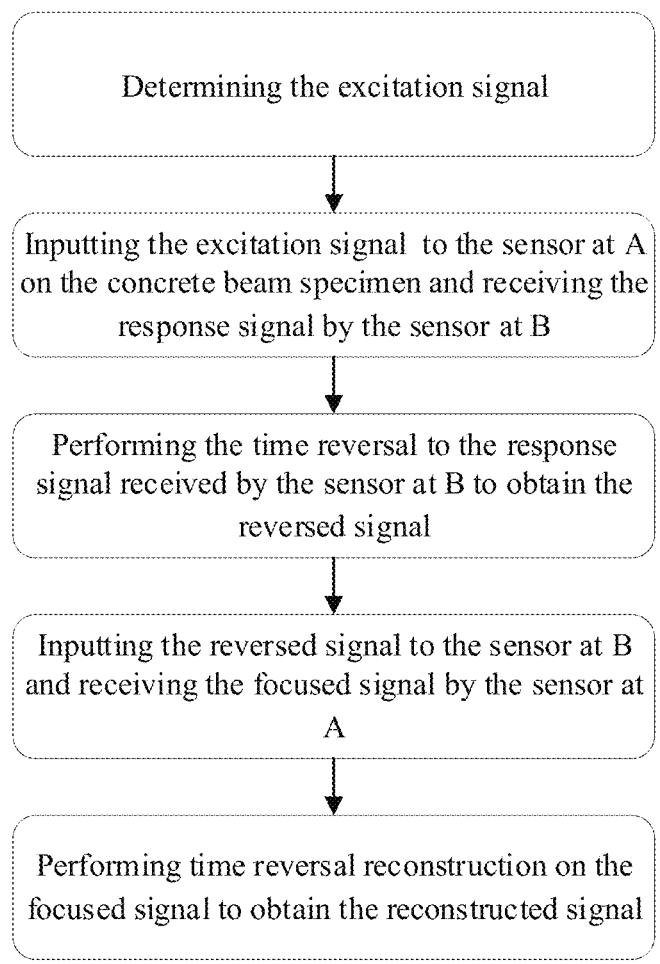
FIG. 5 is a flow chart of the time reversal test in the present invention.
Figure 6:
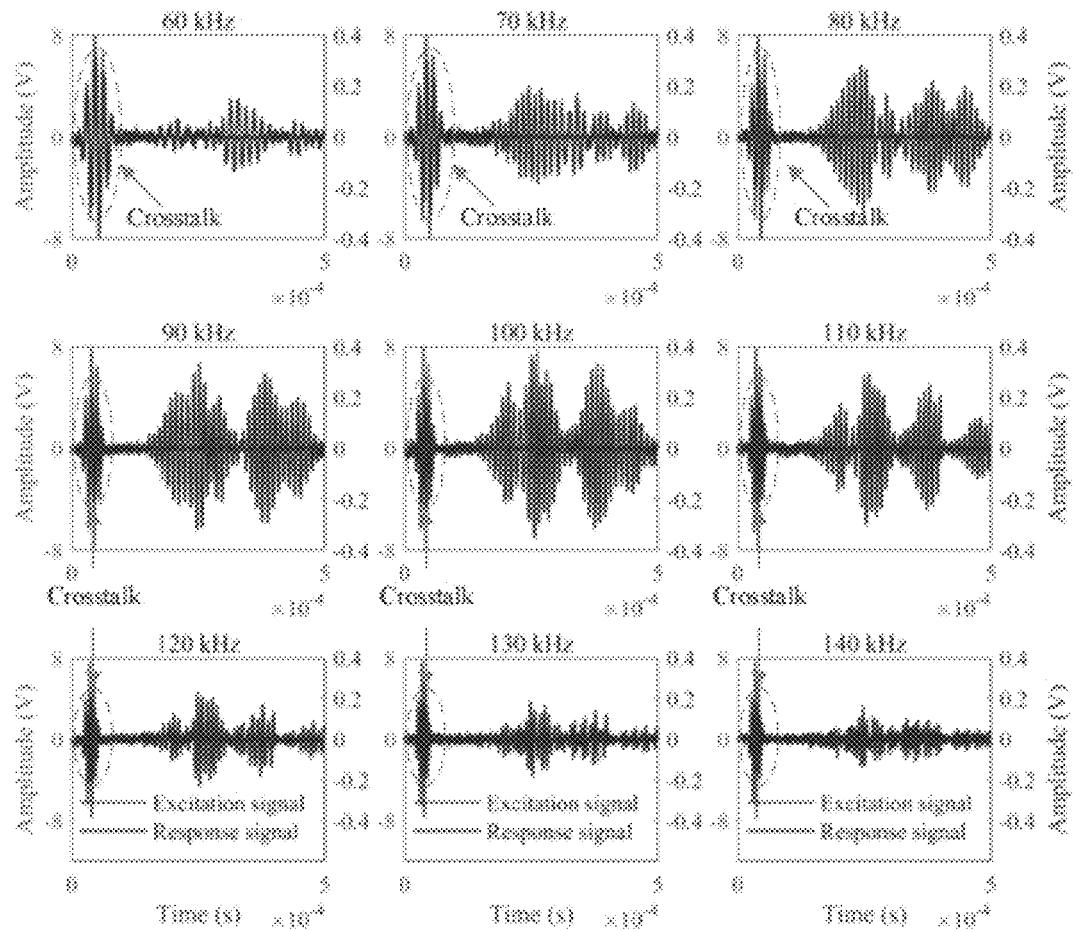
FIG. 6 is a diagram of modulated signals with different central frequencies (60-140 kHz) and corresponding response signals in the present invention.
Figure 7:
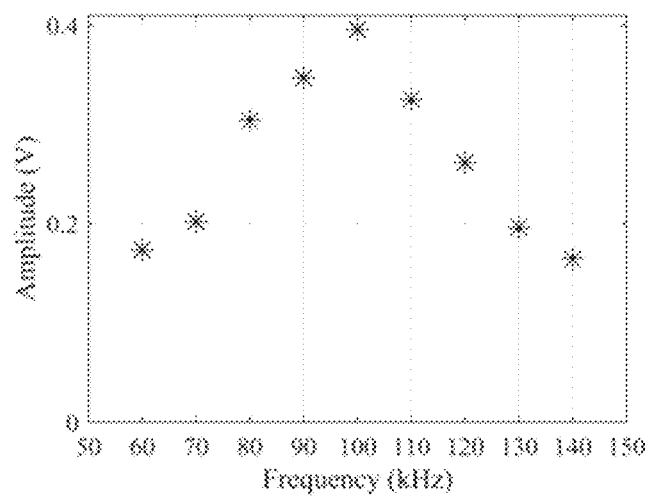
FIG. 7 is a diagram of amplitudes of response signals with different central frequencies (60-140 kHz) in the present invention.
Figures 11A, 11B, 11C, 11D:
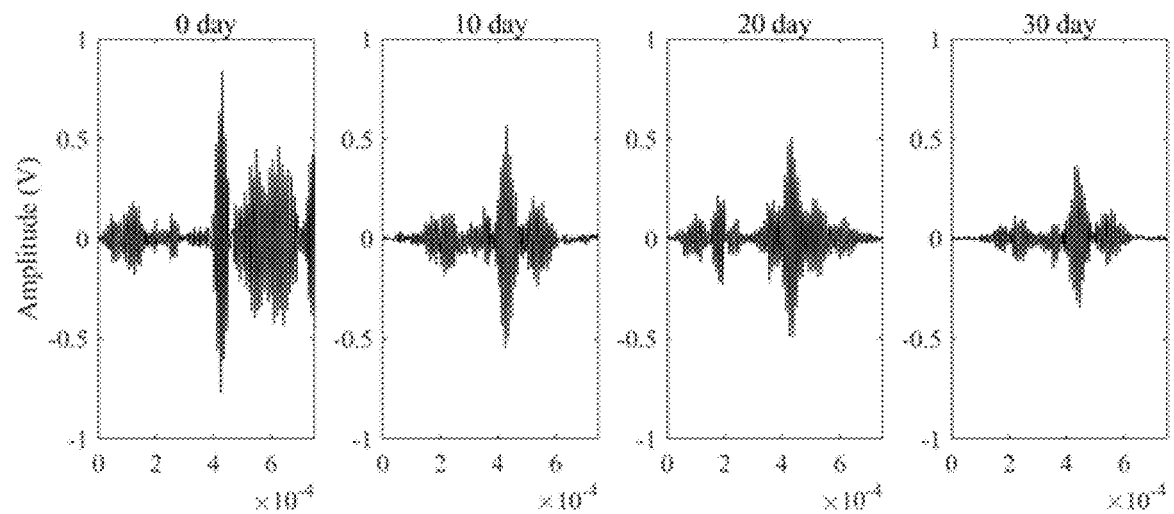
FIGS. 11A-11D are diagrams of the focused signal obtained by performing the time reversal test on the concrete beam specimen at different corrosion durations in the present invention.
Figures 12A, 12B, 12C, 12D:
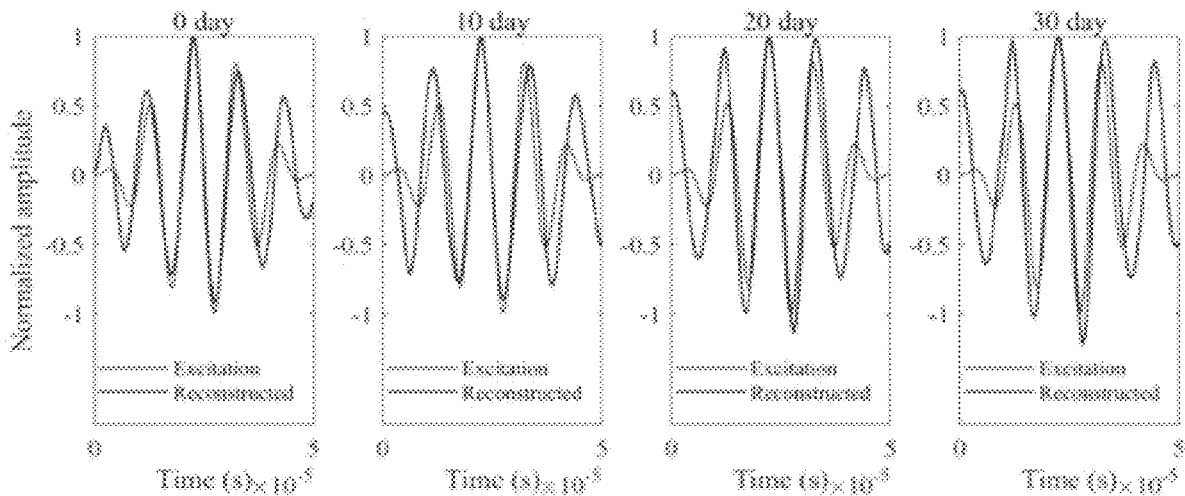
FIGS. 12A-12D are diagrams of the excitation signal and the reconstructed signal obtained by performing the time reversal test on the concrete beam specimen at different corrosion durations and after normalization in the present invention.

(2) after being maintained, immerse the concrete beam specimen and the cube specimens in water for 10 days to achieve a state of full immersion.

next, the time reversal test of stress waves is performed on the concrete beam specimen, before the test, as shown in FIG. 3, two clamps are connected to the two leads ③, the two leads ③ are led out from the sensor ⑤ at A and the sensor ⑥ at B on the concrete beam specimen separately, and the sensor ⑤ at A and the sensor ⑥ at B are preset on the concrete beam specimen.

a process of the time reversal test is shown in FIG. 5, the excitation signal $V_A(t)$ is selected at first, and the method for determining the excitation signal $V_A(t)$ includes:

(3) generating a modulated signal with an amplitude of 8 Vp-p, a center frequency of 0-10 mHz and an interval of 10 kHz of the 5-cycle sine function modulated by a Hanning window by the signal generator, with expression as follows:

$$x(t) = \sin(2\pi f_c t)\left[1 - \cos\frac{2\pi f_c t}{5}\right]$$

in the formula, $f_c$ is the center frequency of the modulated signal, the modulated signal is input to the sensor ⑤ at A on the concrete beam specimen separately, the response signal is received by the sensor ⑥ at B, a waveform diagram of the response signal in a frequency band of 60-140 kHz is shown in FIG. 6, and the maximum amplitude of the response signal is shown in FIG. 7. Selecting the corresponding signal with the maximum amplitude of the response signal, that is, the modulated signal of the 5-cycle sine function modulated by a Hanning window with the central frequency of 100 kHz as the excitation signal $V_A(t)$ for the follow-up test, with time domain and frequency domain as shown in FIGS. 8A-8B.

(4) inputting the excitation signal $V_A(t)$ modulated by the 5-cycle sine function modulated by a Hanning window with an amplitude of 8 Vp-p and a central frequency of 100 kHz is to the sensor ⑤ at A on the concrete beam specimen through the signal generator, propagating stress waves from A to B, and receiving the response signal $V_B(t)$ by the sensor ⑥ at B, with the expression of the response signal in frequency domain as follows:

$$V_B(r,\omega) = k_A(\omega)k_B(\omega)G(r,\omega)V_A(\omega)$$

the expression of the response signal in time domain follows:

$$V_B(t) = \frac{1}{2\pi}\int_{-\infty}^{+\infty} V_B(r,\omega)e^{i\omega t}d\omega$$

In the formula, r is the distance from A to B (that is, the distance of propagation of stress waves), $k_A$ is an electromechanical coupling coefficient of the sensor ⑤ at A, $k_B$ is an electromechanical coupling coefficient of the sensor ⑥ at B, and $G(r, \omega)$ is the transfer function from the sensor ⑤ at A to the sensor ⑥ at B. The response signal obtained in the test is shown in FIGS. 9A-9D, and in this step, the sensor ⑤ at A and the sensor ⑥ at B are used as an exciter and a receiver respectively;

(5) applying a rectangular window to remove the crosstalk from the response signal $V_B(t)$, and then performing the time reversal to obtain the reversed signal $V_B(-t)$, as shown in FIGS. 10A-10D, the expression of the rectangular window function is as follows:

$$w(t) = \begin{cases} 1, & 0 \le t \le T \\ 0, & \text{else} \end{cases}$$

the expression of the reversed signal in frequency domain is:

$$\hat{V}_B(r,\omega) = k^*_A(\omega)k^*_B(\omega)G^*(r,\omega)V^*_A(\omega)e^{i\omega T}$$

the expression of the reversed signal in time domain is:

$$V_B(-t) = \frac{1}{2\pi}\int_{-\infty}^{+\infty} V^*_B(r,\omega)e^{i\omega T}e^{i\omega t}d\omega$$

In the formula, $V^*_B$ is the phase conjugation of $V_B$, * is the complex conjugation operator, T is the sampling duration, and r is the distance from A to B;

(6) inputting the reversed signal in step (5) to the sensor ⑥ at B on the concrete beam specimen, and receiving the focused signal by the sensor ⑤ at A, as shown in FIGS. 11A-11D, the expression of the focused signal in frequency domain is as follows:

$$\hat{V}_A(r,\omega) = k_A(\omega)k^*_A(\omega)k_B(\omega)k^*_B(\omega)G(r,\omega)G^*(r,\omega)V^*_A(\omega)e^{i\omega T}$$

the expression of the focused signal in time domain is:

$$\hat{V}_A(t) = \frac{1}{2\pi}\int_{-\infty}^{+\infty} \hat{V}_A(r,\omega)e^{i\omega t}d\omega$$

$$= \frac{1}{2\pi}\int_{-\infty}^{+\infty} k_A(\omega)k^*_A(\omega)k_B(\omega)k^*_B(\omega)G(r,\omega)G^*(r,\omega)V^*_A(\omega)e^{i\omega T}e^{i\omega t}d\omega$$

(7) performing time reversal reconstruction on the focused signal in step (6) to obtain the reconstructed signal, with the expression of the reconstructed signal in frequency domain as follows:

$$\tilde{V}_A(r,\omega) = \hat{V}^*_A(r,\omega)e^{i\omega T}$$

In the formula, $\hat{V}^*_A$ is the phase conjugation of $\hat{V}_A$, and * is the complex conjugation operator.

the expression of the reconstructed signal in time domain is:

$$\tilde{V}_A(t) = \frac{1}{2\pi}\int_{-\infty}^{+\infty} \hat{V}_A^*(r,\omega)e^{i\omega T}e^{i\omega t}d\omega$$

$$= \frac{1}{2\pi}\int_{-\infty}^{+\infty} k_A(\omega)k_B(\omega)k_A^*(\omega)k_B^*$$

$$(\omega)G(r,\omega)G^*(r,\omega)V_A(\omega)e^{i\omega t}d\omega$$

(8) performing normalization on the excitation signal in step (3) and the reconstructed signal in step (7), with the formula of normalization as follows:

$$N_A(t)=V_A(t)/\max(V_A(t))$$

$$\tilde{N}_A(t)=\tilde{V}_A(t)/\max(\tilde{V}_A(t))$$

In the formula, $V_A(t)$ is the excitation signal, $\tilde{V}_A(t)$ is the reconstructed signal, $N_A(t)$ is the normalized excitation signal, and $\tilde{N}_A(t)$ is the normalized reconstructed signal; and the normalized excitation signal and the normalized reconstructed signal are shown in FIGS. 12A-12D. The damage index can be calculated by substituting the normalized excitation signal and the normalized reconstruction signal into the following formula:

$$DI = 1 - \sqrt{\left[\int_{t_0}^{t_1}N_A(t)\tilde{N}_A(t)dt\right]^2 / \int_{t_0}^{t_1}[N_A(t)]^2dt\int_{t_0}^{t_1}[\tilde{N}_A(t)]^2 dt} \times 100\%$$

In the formula, DI is the damage index, $t_0$ and $t_1$ are start time and end time of the signal comparison interval separately, $N_A(t)$ is the normalized excitation signal, and $\tilde{N}_A(t)$ is the normalized reconstructed signal.

Next, the uniaxial compression test is performed on the concrete cube specimens;

(9) performing the uniaxial compression test on concrete cube specimens to obtain the stress-strain curves to calculate the compressive strength and the elastic modulus of concrete with the following formulas:

$$F_{cp} = \frac{F_{max}}{A}$$

$$E_c = \frac{(F_a - F_0)}{A} \times \frac{L}{\Delta}$$

in the formulas, $F_{cp}$ is the compressive strength of the concrete cube specimen, $F_{max}$ is the failure load, A is the loading area of the specimen, $E_c$ is the elastic modulus of the concrete cube specimen, $F_a$ is the load when stress is $\tfrac{2}{3}F_{cp}$, $F_0$ is the load when stress is $\tfrac{1}{3}F_{cp}$, L is the measuring scale distance of the concrete cube specimen, and $\Delta$ is the deformation of the concrete cube specimen loaded from $F_0$ to $F_a$;

(10) replacing the water in the tank with the hydrochloric acid solution with pH=1, immersing the concrete beam specimen and the cube specimens in the hydrochloric acid solution to introduce corrosion damage, and repeating steps (4) to (9) on the 10th, 20th and 30th days after immersing the concrete beam specimen and the cube specimens in the hydrochloric acid solution, separately, and calculating the damage index, the compressive strength and the elastic modulus of the concrete after corrosion;

(11) using the damage index, the compressive strength and the elastic modulus to calculate the corrosion index, the loss rate of concrete compressive strength and the loss rate of concrete elastic modulus, with the formulas as follows:

$$CI = DI' - DI^0$$

$$LR_F = \frac{F_{cp}^0 - F'_{cp}}{F_{cp}^0}$$

$$LR_E = \frac{E_c^0 - E'_c}{E_c^0}$$

in the formulas, CI is the corrosion index, $DI^0$ is the damage index of concrete in the water-immersed state, DI' is the damage index of concrete in the corrosion state, $LR_F$ is the loss rate of concrete compressive strength, $F_{cp}^0$ is the compressive strength of concrete in the water-immersed state, $F'_{cp}$ is the compressive strength of concrete in the corrosion state, $LR_E$ is the loss rate of concrete elastic modulus, $E_c^0$ is the elastic modulus of concrete in the water-immersed state, and $E'_c$ is the elastic modulus of concrete in the corrosion state.

(12) calculating the absolute error between the corrosion index and the loss rate of concrete compressive strength, and calculating the absolute error between the corrosion index and the loss rate of concrete elastic modulus, with the formulas as follows:

$$\delta_{CF}=CI-LR_F$$

$$\delta_{CE}=CI-LR_E$$

in the formulas, $\delta_{CF}$ is the absolute error between the corrosion index and the loss rate of concrete compressive strength, CI is the corrosion index, $LR_F$ is the loss rate of concrete compressive strength, $\delta_{CE}$ is the absolute error between the corrosion index and the loss rate of concrete elastic modulus, and $LR_E$ is the loss rate of concrete elastic modulus.

Figure 13:
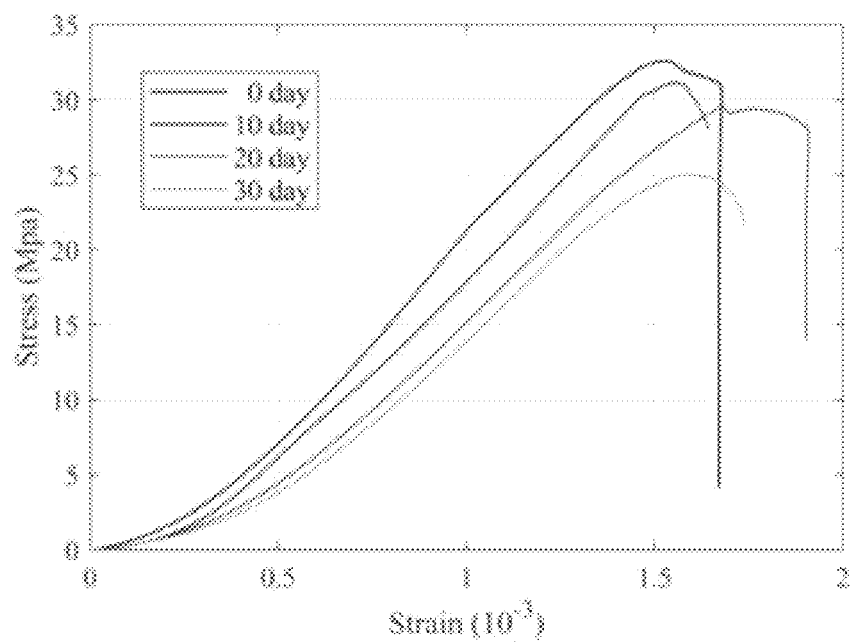
FIG. 13 is stress-strain curves of concrete cube specimens with different corrosion durations obtained from the uniaxial compression test.

FIGS. 12A-12D show the normalized excitation signal and the normalized reconstructed signal, FIG. 13 shows the stress-strain curves of concrete cube specimens with different corrosion durations obtained from the uniaxial compression test, and the above test data are summarized in Table 1 and Table 2 as follows:

TABLE 1

| Corrosion duration t | 0 | 10 | 20 | 30 |
|---|---|---|---|---|
| The loss rate of concrete compressive strength $LR_F$ | 0 | 4.46% | 9.39% | 23.29% |
| Corrosion index CI | 0 | 7.35% | 13.39% | 23.06% |
| The absolute error $\delta_{CF}$ | 0 | 2.89% | 4.00% | 0.23% |

TABLE 2

| Corrosion duration t | 0 | 10 | 20 | 30 |
|---|---|---|---|---|
| The loss rate of concrete elastic modulus $LR_F$ | 0 | 12.11% | 18.03% | 24.08% |
| Corrosion index CI | 0 | 7.35% | 13.39% | 23.06% |
| The absolute error $\delta_{CE}$ | 0 | 4.76% | 4.64% | 1.02% |

It can be seen from Table 1 and Table 2 that the absolute error $\delta_{CF}$ between the corrosion index and the loss rate of concrete compressive strength and the absolute error $\delta_{CE}$ between the corrosion index and the loss rate of concrete elastic modulus are less than 5%, and the corrosion index can reasonably evaluate the corrosion state of concrete. The above results show that the provided method is feasible and effective for evaluating the corrosion damage evolution of underwater concrete structures.

The evaluation method for corrosion damage evolution of underwater concrete structures provided by the present invention timely and effectively represents degradation degree of mechanical properties of the underwater concrete structures caused by corrosion, provides a feasible method for realizing the corrosion damage evolution evaluation of the underwater concrete structure, and the method is practical and worth popularizing.

The examples disclosed above are only preferable specific examples of the present invention, but the examples of the present invention are not limited to the above examples, and variations readily conceivable to anyone skilled in the art all fall within the scope of protection of the present invention.

What is claimed is:

1. An evaluation method for corrosion damage evolution of underwater concrete structures, comprising:
   (a) immersing a concrete beam specimen and a plurality of concrete cube specimens in water to obtain a first immersed concrete beam specimen and a plurality of first immersed concrete cube specimens;
   (b) performing a time reversal test on the first immersed concrete beam specimen in the water to obtain a damage index $DI^0$ of a concrete in a water-immersed state, performing a uniaxial compression test on the plurality of first immersed concrete cube specimens to obtain a compressive strength $F_{cp}^0$ and an elastic modulus $E_c^0$ of the concrete in the water-immersed state;
   (c) immersing the first immersed concrete beam specimen and the plurality of first immersed concrete cube specimens in a hydrochloric acid solution to mimic a long-term corrosion damage of the concrete in the water-immersed state to obtain a second immersed concrete beam specimen and a plurality of second immersed concrete cube specimens, performing the time reversal test on the second immersed concrete beam specimen in the hydrochloric acid solution on 10th, 20th, and 30th days respectively to obtain a damage index $DI'$ of a concrete in a corrosion state, and at the same time, performing the uniaxial compression test on the plurality of second immersed concrete cube specimens on 10th, 20th, and 30th days respectively to obtain a compressive strength $F_{cp}'$ and an elastic modulus $E_c'$ of the concrete in the corrosion state;
   (d) calculating a corrosion index CI with formula (1), calculating a concrete compressive strength loss rate $LR_F$ with formula (2), calculating a concrete elastic modulus loss rate $LR_E$ with formula (3), and $$CI = DI' - DI^0 \tag{1}$$

$$LR_F = \frac{F_{cp}^0 - F_{cp}'}{F_{cp}^0} \tag{2}$$

$$LR_E = \frac{E_c^0 - E_c'}{E_c^0} \tag{3}$$

(e) calculating an absolute error $\delta_{CF}$ between the corrosion index and the concrete compressive strength loss rate with formula (4), and calculating the absolute error $\delta_{CE}$ between the corrosion index and the concrete elastic modulus loss rate with formula (5) to realize an evaluation of the corrosion damage evolution of the underwater concrete structures;

$$\delta_{CF} = CI - LR_F \tag{4}$$

$$\delta_{CE} = CI - LR_E \tag{5}$$

wherein a method for obtaining a damage index of a concrete by performing the time reversal test on the concrete beam specimen comprises:

(21) determining an excitation signal $V_A(t)$;

(22) inputting the excitation signal $V_A(t)$ to a first sensor at position A on the concrete beam specimen, an expression of response signals $V_B$ received by a second sensor at position B in a frequency domain is formula (6), $$V_B(r,\omega) = k_A(\omega)k_B(\omega)G(r,\omega)V_A(\omega) \tag{6}$$

an expression of the response signals $V_B$ in a time domain is formula (7), $$V_B(t) = \frac{1}{2\pi}\int_{-\infty}^{+\infty} V_B(r,\omega)e^{i\omega t}d\omega \tag{7}$$

in the formula, r is a distance from the position A to the position B, $k_A$ is an electromechanical coupling coefficient of the first sensor at the position A, $k_B$ is an electromechanical coupling coefficient of the second sensor at the position B, and $G(r,\omega)$ is a transfer function from the first sensor at the position A to the second sensor at the position B; $V_B(t)$ is the response signals received by the sensor at the position B in the time domain;

(23) applying a rectangular window, as shown in formula (8), to a response signal $V_B$ to remove a crosstalk, and then performing a time reversal to obtain the reversed signal $\hat{V}_B$, $$w(t) = \begin{cases} 1, & 0 \leq t \leq T \\ 0, & \text{else} \end{cases} \tag{8}$$

an expression of a reversed signal $\hat{V}_B$ in the frequency domain is formula (9), $$\hat{V}_B(r,\omega) = k_A^*(\omega)k_B^*(\omega)G^*(r,\omega)V_A^*(\omega)e^{j\omega T} \tag{9}$$

an expression of a reversed signal $\hat{V}_B$ in the time domain is formula (10), $$V_B(-t) = \frac{1}{2\pi}\int_{-\infty}^{+\infty} V_B^*(r,\omega)e^{i\omega T}e^{i\omega t}d\omega \tag{10}$$

in the formulas, $V_B^*$ is a phase conjugation of $V_B$, * is a complex conjugation operator, T is a sampling duration;

(24) inputting the reversed signal $\hat{V}_B$ to the second sensor at the position B, then the first sensor at the position A receives a focused signal $\hat{V}_A$, an expression of the focused signal $\hat{V}_A$ in the frequency domain is formula (11), and $$\hat{V}_A(r,\omega) = k_A(\omega)k_A^*(\omega)k_B(\omega)k_B^*(\omega)G(r,\omega)G^*(r,\omega)V_A^*(\omega)e^{i\omega T} \quad (11)$$

an expression of the focused signal $\hat{V}_A$ in the time domain is formula (12);

$$\hat{V}_A(t) = \frac{1}{2\pi}\int_{-\infty}^{+\infty} \hat{V}_A(r,\omega)e^{i\omega T}d\omega \quad (12)$$

$$= \frac{1}{2\pi}\int_{-\infty}^{+\infty} k_A(\omega)k_A^*(\omega)k_B(\omega)k_B^*$$

$$(\omega)G(r,\omega)G^*(r,\omega)V_A^*(\omega)e^{i\omega T}e^{i\omega t}d\omega$$

(25) performing a time reversal reconstruction on a focused signal $\hat{V}_A$ to obtain a reconstructed signal $\tilde{V}_A$, and an expression of the reconstructed signal $\tilde{V}_A$ in the frequency domain is formula (13), $$\tilde{V}_A(r,\omega) = \hat{V}_A^*(r,\omega)e^{i\omega T} \quad (13)$$

in the formula, $\hat{V}_A^*$ is a phase conjugation of $\hat{V}_A$, and * is the complex conjugation operator; and an expression of a reconstructed signal $\tilde{V}_A$ in the time domain is formula (14);

$$\tilde{V}_A(t) = \frac{1}{2\pi}\int_{-\infty}^{+\infty} \hat{V}_A^*(r,\omega)e^{i\omega T}e^{i\omega t}d\omega \quad (14)$$

$$= \frac{1}{2\pi}\int_{-\infty}^{+\infty} k_A(\omega)k_B(\omega)k_A^*(\omega)k_B^*$$

$$(\omega)G(r,\omega)G^*(r,\omega)V_A(\omega)e^{i\omega T}d\omega$$

(26) performing a normalization on the excitation signal $V_A(t)$ and the reconstructed signal $\tilde{V}_A$ with formula (15), $$N_A(t) = V_A(t)/\max(V_A(t)) \quad (15)$$

in the formulas, $N_A$ is a normalized excitation signal, and $\tilde{N}_A$ is a normalized reconstructed signal; and

(27) substituting the normalized excitation signal $N_A(t)$ and the normalized reconstructed signal $\tilde{N}_A(t)$ into formula (16) to calculate a damage index DI;

$$DI = 1 - \sqrt{\left[\int_{t_0}^{t_1} N_A(t)\tilde{N}_A(t)dt\right]^2 / \int_{t_0}^{t_1}[N_A(t)]^2 dt \int_{t_0}^{t_1}[\tilde{N}_A(t)]^2 dt} \times 100\% \quad (16)$$

in the formula, $t_0$ and $t_1$ are a start time and an end time of a signal comparison interval separately;

wherein a method for determining the excitation signal $V_A(t)$ comprises:

an expression of a 5-cycle sine function modulated by a Hanning window is formula (17), $$x(t) = \sin(2\pi f_c t)\left[1 - \cos\frac{2\pi f_c t}{5}\right] \quad (17)$$

in the formula, $f_c$ is a central frequency of modulated signals;

a method for determining the central frequency $f_c$ of the modulated signals is as follows:

modulating modulated signals with different central frequencies from 0-10 MHz at an interval of 10 kHz, inputting the modulated signals with different central frequencies to the first sensor at the position A on the concrete beam specimen separately, response signals are received by the second sensor at the position B, comparing the response signals and selecting a modulated signal with a largest amplitude of the response signals as the excitation signal $V_A(t)$.

2. The evaluation method for the corrosion damage evolution of the underwater concrete structures according to claim 1, wherein a compressive strength $F_{cp}$ of the concrete is obtained with formula (18), and an elastic modulus $E_c$ of the concrete is obtained with formula (19);

$$F_{cp}^0 = \frac{F_{max}}{A} \quad (18)$$

$$E_c^0 = \frac{(F_a - F_0)}{A} \times \frac{L}{\Delta} \quad (19)$$

in the formulas $F_{max}$ is a failure load, A is a loading area of the concrete cube specimen, $F_a$ is a load when a stress is $\tfrac{2}{3}F_{cp}$, $F_0$ is a load when the stress is $\tfrac{1}{3}F_{cp}$, L is a measuring scale distance of the concrete cube specimen, and $\Delta$ is a deformation of the concrete cube specimen loaded from $F_0$ to $F_a$.

3. The evaluation method for the corrosion damage evolution of the underwater concrete structures according to claim 1, wherein a method for preparing the concrete beam specimen comprises:

performing an anti-corrosion, an insulation, and a waterproof treatment on a pair of sensors;

building a formwork of the concrete beam specimen;

placing the pairs of sensors at predetermined positions in the formwork of the concrete beam specimen; and pouring the concrete, and completing a maintenance according to standards.

* * * * *